(12) United States Patent
North

(10) Patent No.: US 8,720,447 B2
(45) Date of Patent: May 13, 2014

(54) SUSPENDED BACK PILLOW FOR SUSTAINING A SIDE SLEEPING POSITION

(75) Inventor: Vaughn W. North, Salt Lake City, UT (US)

(73) Assignee: Family Concepts TJH, LLC, Salt Lake City, UT (US)

( * ) Notice: Subject to any disclaimer, the term of this patent is extended or adjusted under 35 U.S.C. 154(b) by 425 days.

(21) Appl. No.: 12/975,144

(22) Filed: Dec. 21, 2010

(65) Prior Publication Data

US 2011/0179573 A1 Jul. 28, 2011

Related U.S. Application Data

(63) Continuation-in-part of application No. 12/581,732, filed on Oct. 19, 2009, now Pat. No. 8,429,775, and a continuation-in-part of application No. 12/490,143, filed on Jun. 23, 2009, now Pat. No. 7,874,032.

(51) Int. Cl.
 *A47C 20/00* (2006.01)
 *A47G 9/10* (2006.01)
 *A61F 5/37* (2006.01)

(52) U.S. Cl.
 USPC .................. 128/845; 5/630; 5/633; 128/871; 128/869

(58) Field of Classification Search
 USPC .............. 128/846, 848, 871; 2/115, 125, 127, 2/133; 5/424, 630, 632, 655
 See application file for complete search history.

(56) References Cited

U.S. PATENT DOCUMENTS

| | | | |
|---|---|---|---|
| 2,304,235 A | 12/1942 | Boots | |
| 2,562,725 A | 7/1951 | Leto et al. | |
| 2,629,884 A | 2/1953 | McMonagle | |
| 2,765,480 A | 10/1956 | Mueller | |
| 2,952,856 A | 9/1960 | Ruff | |
| 3,485,241 A | 12/1969 | Polley | |
| 3,924,282 A | 12/1975 | Bond | |
| 4,274,673 A | 6/1981 | Kifferstein | |

(Continued)

FOREIGN PATENT DOCUMENTS

EP 2130459 12/2009

OTHER PUBLICATIONS

Rematee Positional Sleeping Solutions for Sleep Apnea, Maternity, Snoring; 2009; 4 pages.
U.S. Appl. No. 12/898,556, filed Oct. 5, 2010; Vaughn W. North.

(Continued)

*Primary Examiner* — Tatyana Zalukaeva
*Assistant Examiner* — Tarla Patel
(74) *Attorney, Agent, or Firm* — Thorpe North & Western LLP

(57) ABSTRACT

A device and method for enabling an individual located on a bed to sustain a side-sleeping orientation on either a left or right side. The device comprises a light weight, elongate pillow having a longitudinal axis and being configured to concurrently rest at a back side of the individual and an adjacent surface of a bed when reclined in a side-sleeping orientation on the bed. The pillow includes a flexible attachment structure which is positioned along a longitudinal edge of the pillow to secure the pillow to the individual's bed clothing. The attachment structure provides sufficient flexibility to allow the pillow to rotate with respect to and rest against the individual's back to a laterally offset and suspended, partial captured configuration in general alignment with the individual's spine and in concurrent contact with the bed surface to prevent a supine sleeping position.

18 Claims, 9 Drawing Sheets

(56) References Cited

U.S. PATENT DOCUMENTS

| | | |
|---|---|---|
| 4,506,396 A | 3/1985 | Ritchie et al. |
| 4,528,981 A | 7/1985 | Behar |
| 4,744,117 A | 5/1988 | Bond |
| 4,754,509 A | 7/1988 | Pollard |
| 5,040,546 A | 8/1991 | Deluhery |
| 5,044,026 A | 9/1991 | Matthews |
| 5,165,130 A | 11/1992 | Wending |
| 5,182,828 A | 2/1993 | Alivizatos |
| 5,189,748 A | 3/1993 | Garrusin et al. |
| 5,193,238 A | 3/1993 | Clute |
| 5,216,772 A | 6/1993 | Clute |
| 5,272,780 A | 12/1993 | Clute |
| 5,289,748 A | 3/1994 | Kuchta et al. |
| 5,310,245 A | 5/1994 | Lyszczasz |
| 5,341,531 A | 8/1994 | Straub et al. |
| 5,347,669 A | 9/1994 | Neviaser et al. |
| 5,359,739 A | 11/1994 | Rains et al. |
| 5,367,730 A | 11/1994 | Sher |
| 5,499,418 A | 3/1996 | Tan et al. |
| 5,522,104 A | 6/1996 | Little |
| 5,530,941 A | 7/1996 | Rains et al. |
| 5,530,974 A | 7/1996 | Rains et al. |
| 5,535,467 A | 7/1996 | Ciske |
| 5,581,832 A | 12/1996 | Bridley |
| 5,754,998 A | 5/1998 | Selton |
| 5,910,080 A | 6/1999 | Selton |
| 6,009,873 A | 1/2000 | Neviaser |
| 6,067,679 A | 5/2000 | Rice |
| 6,081,950 A | 7/2000 | Selton |
| 6,381,787 B1 | 5/2002 | Rogone et al. |
| 6,560,800 B1 | 5/2003 | Draves |
| 6,640,366 B1 | 11/2003 | Draves |
| 6,698,432 B2 | 3/2004 | Ek |
| 6,877,176 B2 | 4/2005 | Houghteling |
| 6,886,201 B1 | 5/2005 | Weiss-Lohrei |
| 6,954,954 B2 | 10/2005 | Stelnicki |
| 6,971,715 B2 | 12/2005 | Hankins |
| 7,107,635 B2 | 9/2006 | Henry et al. |
| 7,117,553 B2 | 10/2006 | Fairchild et al. |
| 7,134,435 B2 | 11/2006 | Scott |
| 7,240,384 B2 | 7/2007 | DuDonis |
| 7,360,265 B2 | 4/2008 | Lamer |
| 7,874,032 B2 | 1/2011 | North et al. |
| 8,429,775 B2 * | 4/2013 | North ................. 5/633 |
| 2001/0015208 A1 | 8/2001 | Konishi |
| 2003/0200590 A1 | 10/2003 | Haskell |
| 2004/0031492 A1 | 2/2004 | Kawamura |
| 2007/0256695 A1 | 11/2007 | Crocetti |
| 2008/0092297 A1 | 4/2008 | Davis et al. |
| 2008/0222813 A1 * | 9/2008 | Aikman ............. 5/632 |
| 2009/0038077 A1 | 2/2009 | Han et al. |
| 2009/0229054 A1 | 9/2009 | Yates et al. |
| 2009/0229618 A1 | 9/2009 | Sotelo et al. |
| 2009/0313760 A1 | 12/2009 | Blake et al. |
| 2010/0088824 A1 | 4/2010 | Tanner |
| 2010/0319131 A1 | 12/2010 | North |

OTHER PUBLICATIONS

U.S. Appl. No. 11/495,497, filed Jul. 28, 2006; Vaughn W. North; office action issued Feb. 18, 2011.

PCT Application PCT/US2011/065933; filed Dec. 19, 2011; Vaughn W. North; ISR mailed Mar. 28, 2012.

U.S. Appl. No. 12/581,732, filed Oct. 19, 2009; Vaughn W. North; office action dated Aug. 2, 2012.

U.S. Appl. No. 12/898,556, filed Oct. 5, 2010; Vaughn W. North; office action dated Nov. 21, 2012.

* cited by examiner

SUSPENDED BACK PILLOW FOR SUSTAINING A SIDE SLEEPING POSITION

This application is a continuation in part of United States patent application Ser. No. 12/581,732 filed Oct. 19, 2009. This application is also a continuation in part of U.S. patent application Ser. No. 12/490,143 filed Jun. 23, 2009, which is incorporated by reference in its entirety herein.

BACKGROUND OF THE INVENTION

1. Field of the Invention

The present invention relates generally to a method for assisting a person to regulate sleeping positions during a semi-conscious or unconscious state, such as to remain on a side while sleeping and thereby avoid sleeping in a supine position.

2. Related Art

Sleep positional orientation may be an important factor for many persons in preserving health. For example, the typical dominant period of healing for the human body occurs during sleep. Similarly, periods of illness or recovery often require additional rest that involves extended bedtime and sleep. During times of sleep, semi-consciousness or unconsciousness, the position of the body is seldom within the person's conscious awareness. One may be changing positions among basic orientations of lying on one's back, left side, right side, and front. In addition, there are transitional positions between each of these basic positions (partially on back and left side, etc) that further define a near continuum of position orientations for the human body while in a bed-rest condition.

It is recognized that certain body positions may be preferred or even required during sleep and rest for effective health recovery and/or health maintenance. For example, persons having sleep apnea are more vulnerable to disruption of sleep when lying in a back or supine orientation, as compared to sleeping on a side. Similarly, individuals with a snoring problem may be less inclined to snore when in a side-sleeping position. In addition, relative physical positioning of parts of the body may be important, such as when one has a shoulder injury, spine misalignment, hip problem, etc. Even the process of aging may be affected by disposing the body in particular sleep or rest orientations that avoid stressing certain muscle groups and skeletal relationships. In short, a system or methodology of facilitating and controlling a more healthy positional orientation during sleep or rest would be beneficial.

SUMMARY OF THE INVENTION

The present invention is a device and method for enabling an individual located on a bed to sustain a side-sleeping orientation on either a left or right side. The device comprises a light weight, elongate pillow having a longitudinal axis and being configured to rest at a back side of the individual when reclined in a side-sleeping orientation on the bed. The pillow includes attachment structure positioned along a longitudinal edge of the pillow to secure the pillow to the individual. One or more positioning straps can be attached and fixed to the pillow to assist in proper positioning about the trunk of the individual. The attachment structure provides sufficient flexibility to allow the pillow to bi-directionally rotate with respect to and rest against the individual's back to a laterally offset and suspended configuration in general alignment with the individual's spine. The method may be practiced in accordance with the parent patent application which defines a positional sleep orientation aspect (POSA) procedure of positional therapy using at least three contact points of reference to acclimate an individual to sleeping on a side, rather than in supine position. Once so acclimated, stage two is accomplished by attaching the light weight, elongate pillow at the back side of the individual in a suspended configuration, with a longitudinal axis of the pillow substantially aligned with the individual's spine and in a manner that simulates contact between the individual's back side and the first pillow as experienced during sleep in the first stage method of POSA. The individual is then positioned in a side-sleeping orientation on the bed and with pillow contact laterally offset from the spine between the back side of the trunk portion and the pillow, thereby facilitating capture of the pillow between the bed and back side of the individual upon attempted rotation of the body to a supine sleeping position. This position and similar side-sleeping positions are sustained with the laterally offset contact of the light weight pillow over a sufficient period of time prior to and during sleep to establish a sustainable recognition and awareness to the individual of being in the side-position orientation. By positioning the pillow at the individual's spine, a bi-directional hinge aspect can be achieved allowing the same pillow to function on both the right and left sides of the individual.

Other objects and features of the present invention will be apparent to those skilled in the art from the following detailed description, taken in combination with the accompanying drawings.

EMBODIMENTS OF THE INVENTION

Figure 1:
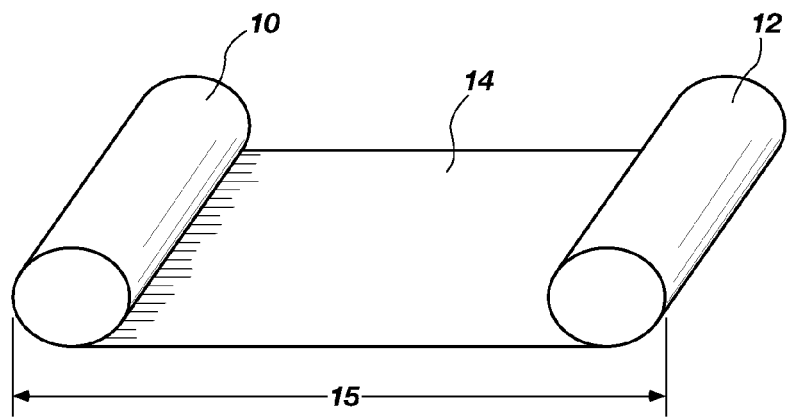
FIG. 1 illustrates a perspective view of a dual pillow system as disclosed in the parent patent application, including two opposing pillows tethered to an intermediate member.

The parent patent application described a method and device involving a pair of opposing pillows tethered together in accordance with concepts represented by an invention referred to as Positional Orientation Sleep Aspect (POSA). Under normal circumstances, a person moves through various sleeping positions (right or left side and back or front) in a random manner. This mobility is an important factor for a healthy sleep experience. It is generally undesirable, therefore, to limit the body to one sleeping position such as may occur by simply imposing pillows snuggly at front and back sides of the individual in a restraining manner. Although positioning a pillow at a single side of an individual can initially place the individual in a preferred side position, once the body moves away from the pillow, its positioning value is substantially compromised.

Positional Orientation Sleep Aspect (POSA) is a methodology and pillow system (FIG. 1) which helps a person achieve desired side sleeping positions without excessive restriction of movement. It utilizes an arrangement of pillows 10 and 12 having a limited width 15 and being coupled together by an intermediate member 14. This pillow system may be viewed as an ongoing sleep aid, or alternatively as a position conditioning tool as part of positional therapy, assisting an individual to form a new habit of sleeping on a side rather than in a supine position. As used in this application, reference to "side" will usually refer to a lateral portion of the individual's trunk, as opposed to the front and back of the individual. References to "front side" or "back side" should be understood to mean the front and back of the individual, as opposed to the lateral sides corresponding to the location of the arms.

A typical sleeping environment is a bed 20 (FIG. 2) or other substantially flat surface which supports the body of the individual in a generally horizontal plane. In this sense, the contact surface of the bed is one-dimensional in that the individual's body has a single side of contact—be it the front, back or one of opposing sides. This one-dimensional contact is acceptable during periods of being awake because the individual can simply make a mental decision to remain in the side-sleeping orientation. Being alert prior to sleep, the individual simply chooses his body position. As he falls into a state of sleep, however, he typically loses this sense of awareness. In a semi or subconscious state, the individual typically moves about without this mental awareness and is not able therefore to control a positional preference.

Over time, an individual may acclimate to various positional tendencies, such as sleeping on one's side or back, and these tendencies may even become somewhat habitual. Unfortunately, those individuals having a habitual tendency to sleep on their back may find themselves more prone to snoring or other breathing problems such as sleep apnea. In these situations, the need to shift from sleeping on one's back to a side-sleeping orientation has been very difficult to achieve. Strategies have usually involved physically forcing the individual to assume the desired position. Specifically, the use of restraining pillows and devices compressed against the body that thereby block movement have often been required. Some sleep apnea patients have been encouraged to place a tennis ball or other stiff object on their back, to discourage a supine position. However, this method is both uncomfortable and physiologically problematic. With methods involving the attachment of a ball or other stiff object to a central back location by pockets, straps or to a night gown or pajama top, physiological discomforts are likely. For example, if the individual attempts to roll onto his back, the ball creates irritation or discomfort under the back. Although the ball prevents supine repositioning, the person is typically aroused and may have difficulty returning to sleep.

With respect to the use of foam pad or other padded devices attached to the person's back, the user experiences discomfort from captured body heat or simply persistent contact of the object against his back while lying on one side. Although seemingly incidental at any given moment, prolonged contact over a large surface area or sustained weight against the back becomes the focus of mental attention to the individual and ultimately may be perceived as an uncomfortable nuisance.

Although prior art efforts to suspend objects at a person's back seem harmless, the above mentioned issues eventually discourage their continued use. This is particularly true if the person is not comfortable with sleeping on their side, but prefers sleeping on their back. Upon falling asleep, he may unconsciously assume that supine position out of habit—increasing the adverse conditions of sleep apnea or snoring.

As mentioned above, the seemingly minor discomfort of a back-mounted device can also become a psychological irritant. For example, the weight of the object resting or hanging against the person's back in a side orientation may become distracting and annoying. Even a nominal weight becomes uncomfortable after several minutes. For a person trying to relax and fall asleep, the slight pressure of the object at one sustained location becomes the focus of attention. After several minutes, the nominal pressure of the object becomes significant and eventually very uncomfortable. The person soon finds himself trapped between two unfavorable options—a side position with the ongoing attached object lying against his back, or a supine position where the object is captured between his back and the bed surface in an unacceptable and sometimes painful location.

The captured position of the object (tennis ball, foam structure or other stiff support device) also creates several physiological problems that trigger a threat response to the body. For example, a tennis ball captured under the back will bear the weight of the individual on a localized, minimal surface area, causing significant pain or discomfort. Theoretically, the prior art deemed this threat response to be a positive effect, in that it would alert the individual to rotate back to a side position. Unfortunately, this type of therapy is physically annoying to the individual, and generates a negative attitude or disposition. The use of a foam pad suspended by straps or a harness also gives rise to discomfort from their confining nature as well as the natural response of the body to sweat from captured body heat at the foam pad contact surface. The pad may also have an abrupt edge that results in localized pressure in a similar manner. As a consequence, the individual may readily abandon the positional therapy. From an emotional or mental perspective, both the captured and suspended configurations of the object against the back simply become one more stress element that inhibits a relaxed state of mind for restful sleep.

Figure 5:
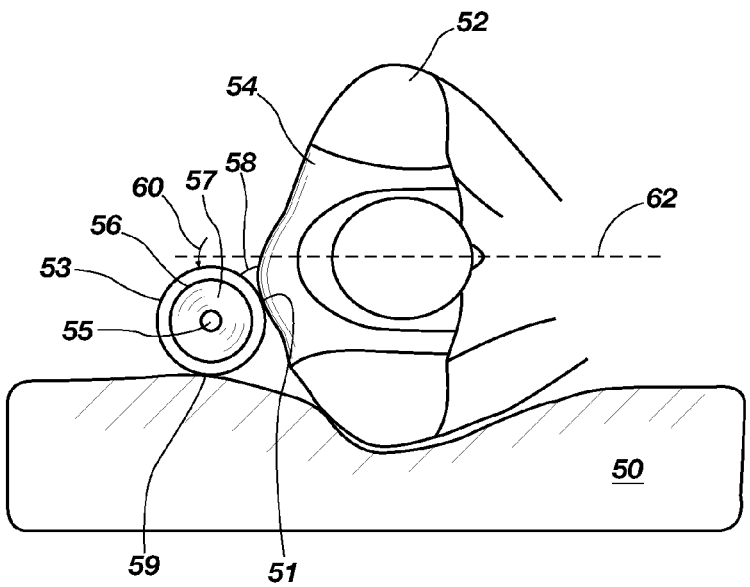
FIG. 5 shows a plan, top end view of the back pillow illustrating a hinged configuration as part of a night shirt.
Figure 10:
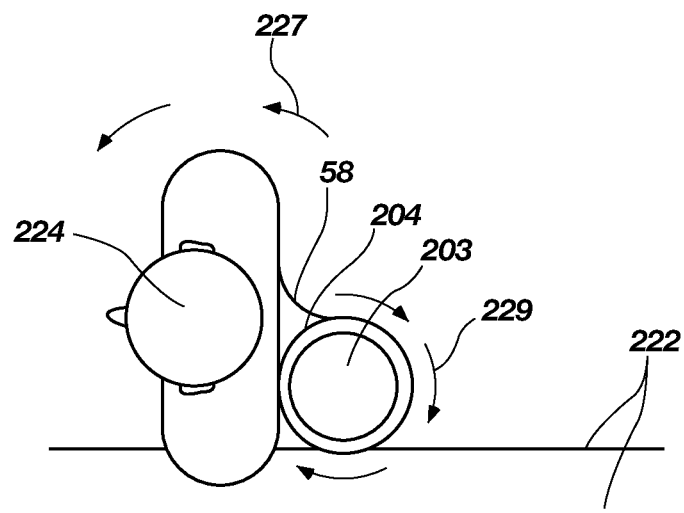
FIG. 10 is a prior art diagram of a rotation of the pillow sleeve as a user rolls toward a side position.

The present invention provides a hinge type structure which enables the back pillow to assume resting position on the bed which is neither fully captured nor suspended, but is supported at the person's back while also resting on the bed surface as shown in FIGS. 5 and 10. This condition is referred to hereafter as "partial" capture of the pillow, in contrast to a full capture in which the person is lying on the pillow under his back (as in a supine or partial supine position). It is characterized by an absence of compressive or strong pressure on the back, yet sufficient contact to enable the individual to at least be aware of its presence. This partial capture reduces the contact irritation with the back as indicated above, while still blocking the individual from rolling to a supine position.

This concept can also be adapted to the POSA method for enabling an individual to mentally sustain a favorable inclination for a desired sleeping position rather than being physically forced to do so. Applying this invention to a sleep environment allows the person to move through a variety of positions with substantial freedom, yet maintain a preference for the desired side-sleeping orientation. This is accomplished by developing a frame of reference for the mind and body based on a positional orientation sleep aspect (POSA). This is realized with a three-dimensional frame of reference to the body through appropriate contact points in a three-dimensional domain. Specifically, by establishing and maintaining at least two respective contact points at the forward and back sides of the individual, in addition to a third point of contact of the person on the bed surface, an increased mental awareness of the body's orientation can be sustained, despite the unconscious state of the individual during sleep. Case studies applying POSA to medical patients have suggested that this awareness may operate even while moving through various changing positions, ultimately returning the individual to a desired side-sleeping orientation.

The first point of reference in the POSA is contact of the trunk portion of the individual in the side-position orientation on the bed as shown in the figures. This naturally occurs based on the body being on the bed surface. Normally, this contact would extend along the length of the person, such as from the head, through the trunk and legs, down to the feet. This is referred to as a single point of contact, however, because in the frame of reference, it constitutes a single side of the individual. In the present invention, a primary interest is to establish either the right or left side of the individual as the first point of contact. In other words, the first point of reference is contact of the body in the side-position orientation on the bed. Because the present invention uses a pillow combination (FIGS. 1 and 2) comprising opposing first and second pillows 10 and 12 tethered between an intermediate member 14 positioned on the bed 20, the actual contact of the individual includes contact of a trunk portion of the body with the intermediate member 14 on the bed.

A second point of reference is contact of a back side 13 of the trunk portion with an adjacent side of the first pillow 10. This contact may be at the shoulders or hips, and any point there between. The nature of the contact arises from the stiffness and size of the pillow. The pillow needs to be sufficiently stiff to resist the weight of the body against it, yet soft enough to be comfortable to body contact.

It is desired that the pillow be sufficiently large in diameter to impede movement of the body over the pillow. Typically, at least a three inch diameter is desired; however, users have discovered that larger diameter pillows can be used as needed, particularly for obese patients. Individual preference is typically determined by balancing the minimal size needed to restrain movement of the user with the maximum size that can be managed conveniently for (i) pillow placement, (ii) maneuvering the individual to and from the pillow combination, and (iii) convenient storage of the device. A variety of sizes will be practical, when considering these minimum and maximum size considerations for different sized individuals.

The pillow also needs to be sufficiently stiff and resilient such that it does not overly compress under weight of the body and can thereby support and resist the second contact point of the POSA. Various pillow materials are available to meet this requirement and have been discussed in the parent application. Inflatable bladders are particularly well suited for the pillow and include inflated air pillows or even balloons. These offer the advantage of adjustable stiffness, based on a variable degree of inflation of the pillow. They are also light in weight and do not bear against the body in the manner will a heavier pillow. This light-weight comfort of the inflatable pillow may be a significant factor for persons that are sensitive to objects against their body.

A further advantage of the inflated pillow is dissipation of body heat that is captured at the contact point of the pillow with the individual's back. An inflated pillow allows transfer of body heat to air or gas contained within the pillow and typically provides a more comfortable temperature environment for the user. In contrast, foam pillows, down inserts and other highly insulative materials can trap body heat and cause a person to sweat during the night. Finally, the air bladder offers the advantage of deflation. Specifically, it can be deflated for transport or storage and therefore offers the benefit of a smaller shipping or storage space.

A third contact reference point for the POSA as described in the parent application includes contact of a forward projecting limb (arm or leg) of the individual with the second pillow 12. This contact may be with a knee 40, 42 in FIG. 3 or an elbow in a restraining configuration with the opposing pillows at maximum separation based on forceful resistance supplied by the fixed length of the thigh or upper arm, or a relaxed contact with less force between the second pillow and a lower leg or foot, and/or forearm or hand.

Figure 2:
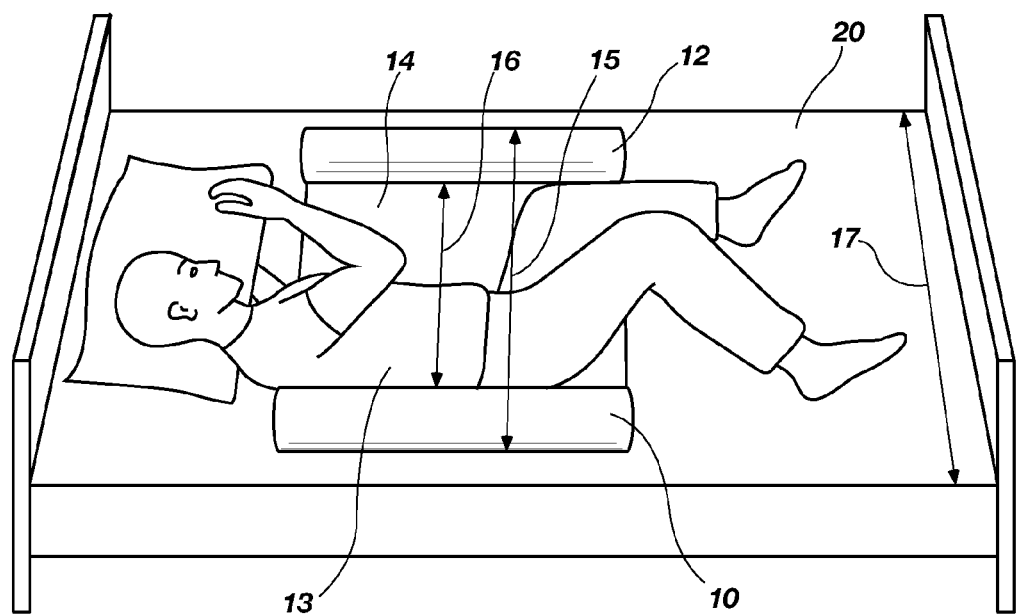
FIG. 2 depicts a graphic, perspective view of the invention in use on a bed with the pillow system fully extended.
Figure 3:
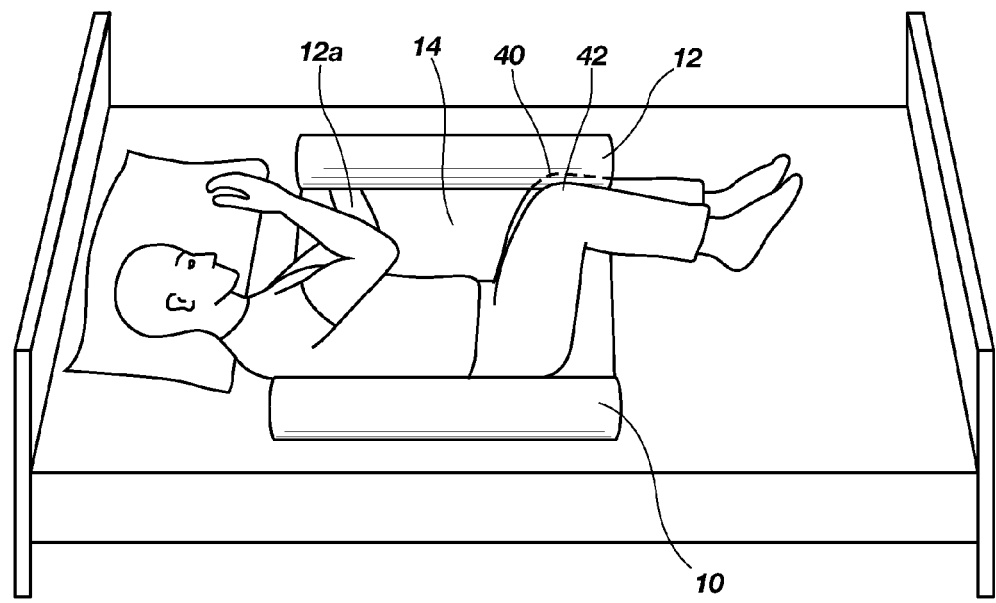
FIG. 3 illustrates in perspective an individual using the dual pillow system in a captured position between his knees.
Figure 4:
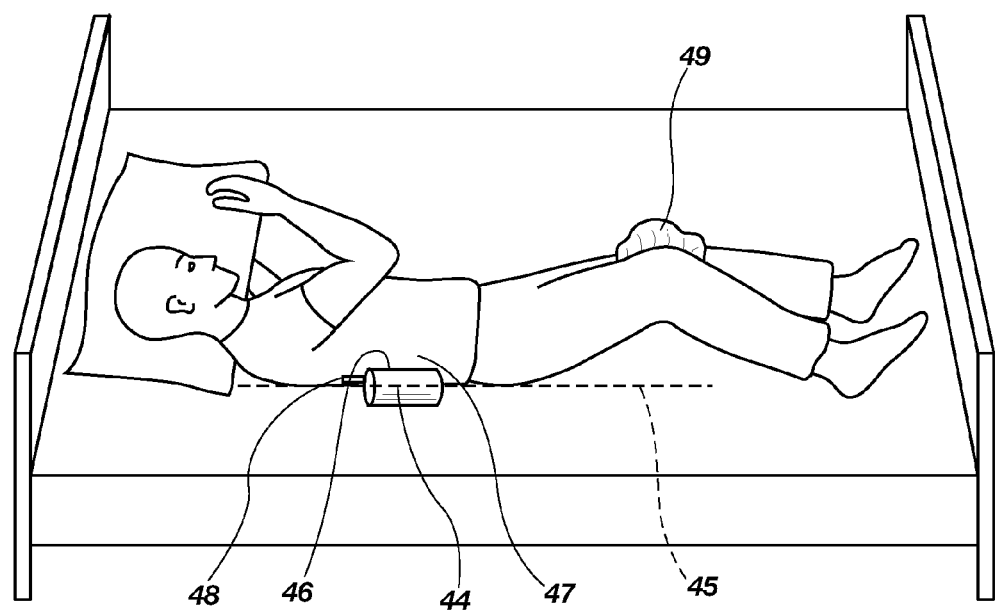
FIG. 4 represents a perspective view of a suspended back pillow for limiting rotation of a person in bed from assuming a supine position.

FIG. 4 illustrates this third point of contact with a knee pillow 49, which has been shown to be particularly helpful after the person is conditioned to sleeping on their side with some form of knee contact 40/42 as illustrated in FIG. 3. In this embodiment, however, the person is using a back pillow 44 in combination with the knee pillow as a substitute for the dual pillow system of FIGS. 1-3. This is explained in detail hereafter.

Specifically, the parent application teaches that a person can become acclimated to sleeping on one side by maintaining the three points of reference of the POSA system during normal sleep. Over a period of time, this side-sleeping position can become a psychologically preferred position and may thereby actually work to the benefit of the user's health. The combination of back pillow and knee pillow can thereby serve as a simulation of the full POSA system represented by FIGS. 2 and 3. Specifically, the mind and body respond to the contact at the back pillow 44, in combination with the pillow contact at the knees 49, such that the three points of reference are satisfied and the body perceives that it is in the preferred side-sleeping position. The result is that the mind and body are both psychologically and physiologically satisfied within the POSA objective of having forward and rearward contact points as a frame of reference. In accordance with prior habitual side sleeping patterns realized within the dual pillow system of FIGS. 1 and 2, the user feels secure and remains on his side.

The advantage of the back pillow configuration is that it is much smaller and more comfortable to use. An individual is also able to more easily occupy a bed with a partner and get in and out of bed without the limitations of the dual pillow structure as part of the bed surface. In essence, the person carries the positioning back pillow on his back without having to consciously manage its positioning or disposition as with the dual pillow system. Because of this, the individual is more likely to permanently continue the positional therapy of maintaining a side-sleeping orientation with the attendant benefits of improved cardiovascular health.

Figure 9:
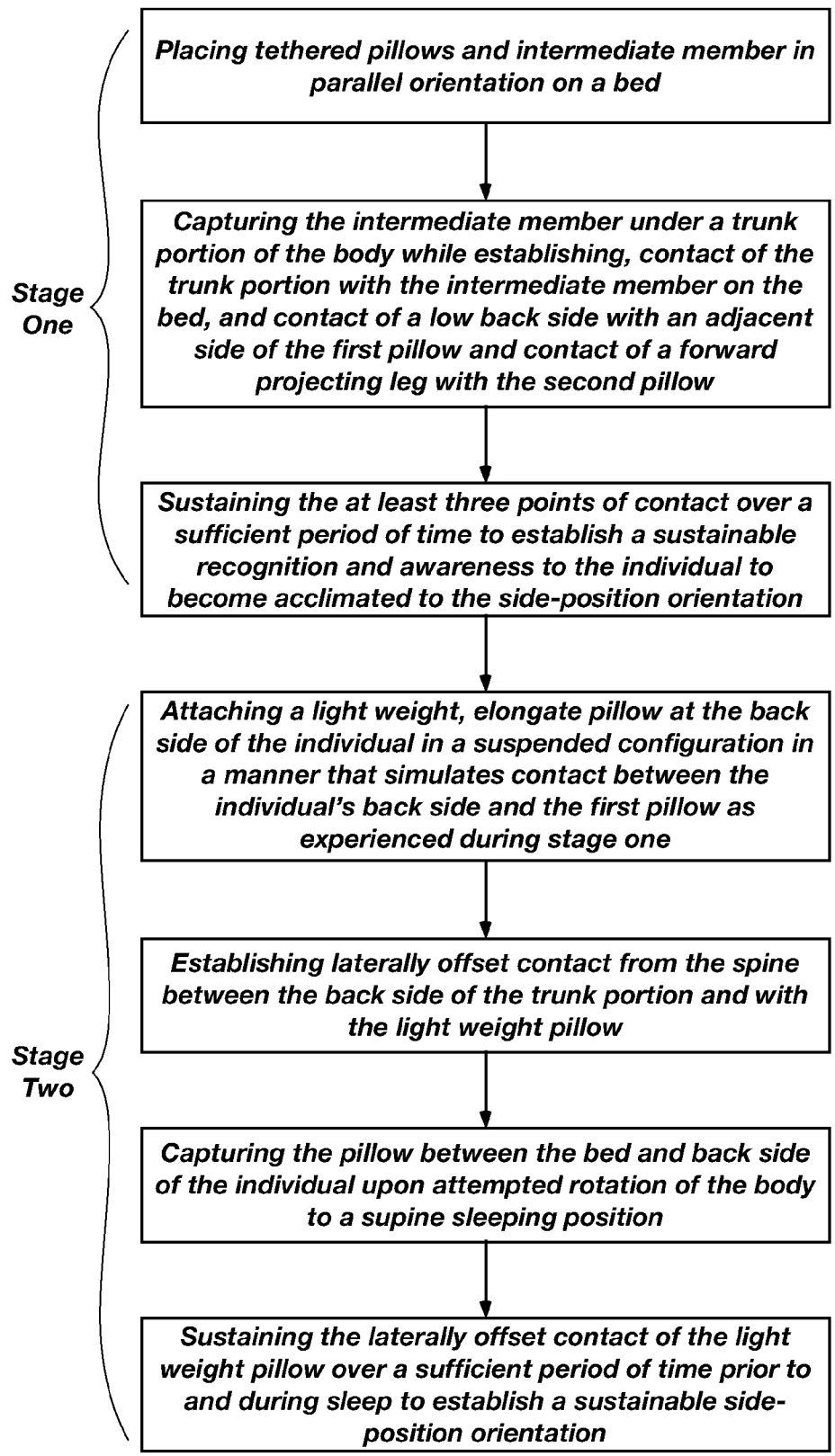
FIG. 9 illustrates one method of practicing the present invention.

Turning to the specific features and methods of the present invention, FIGS. 1 through 3 illustrate the basic dual pillow system as used in the aforementioned POSA methodology. This is summarized as a method for developing a positional orientation sleep aspect (POSA) to enhance individual awareness of sleeping position to enable the individual located on a bed 20 of fixed width 17 to assume at least one preselected side-sleeping orientation alternately on either a left or right side. The method involves two stages of physical assistance using pillows in the following method as illustrated in FIG. 9:

Stage one, utilizing a pillow combination having a full transverse span 15 shorter than the fixed width 17 of the bed and including first and second elongate pillows tethered together at a separation distance 16 in parallel orientation by an intermediate member 14 for providing concurrent support at forward and back sides of the individual, stage one method comprising steps of:

a) placing the tethered pillows 10 and 12 on the bed 20 with the tethered pillows in the parallel orientation;

b) positioning the individual's body in a preselected, side-position orientation on the intermediate member to capture the intermediate member under a trunk portion 13 of the body while establishing at least three separate and concurrent points of contact including (i) contact of the trunk portion in the side-position orientation with the intermediate member 14 on the bed, (ii) contact of a back side 13 of the trunk portion with an adjacent side of the first pillow 10, and (iii) contact of a forward projecting leg from the trunk portion with the second pillow 12;

c) sustaining the at least three points of contact over a sufficient period of time prior to and during sleep to establish a sustainable recognition and awareness to the individual during sleep to become acclimated to the side-position orientation while allowing the individual freedom of movement to also assume alternate positions between the pillow combination, including free movement of the individual's limbs; and Stage two, to commence following the individual becoming acclimated to sleeping in the side-position orientation, comprising the subsequent steps of:

d) attaching a light weight, elongate pillow 44 at the back side of the individual in a suspended configuration, with a longitudinal axis 45 of the pillow substantially aligned with the individual's spine and in a manner that simulates contact between the individual's back side and the first pillow 10 as experienced during sleep in the first stage method of POSA;

e) positioning the individual's body in the preselected, side-position orientation on the bed and having body contact laterally offset from the spine between the back side of the trunk portion 47 with the pillow;

f) partially capturing the pillow between the bed and back side of the individual upon attempted rotation of the body to a supine sleeping position; and g) sustaining the laterally offset contact of the light weight pillow over a sufficient period of time prior to and during sleep to establish a sustainable recognition and awareness to the individual of being in the side-position orientation.

Reference to "laterally offset contact" relates to the relative position of back contact of the pillow 44 with respect to the spine and the bed surface. Specifically, that portion of the back of the individual which is between the side of the body lying on the bed and the back portion proximate to the spine is referred to as the "laterally offset" portion of the back along area 47 extending from the waist to the shoulder area. Corresponding positions would occur on both sides of the individual, to the left and right of the spine.

It should be noted in FIGS. 2 and 3 that the first pillow 10 contacts this laterally offset portion of the back or trunk of the individual when sleeping on a side. During the process of positional therapy in the POSA method, the individual becomes accustomed to pillow contact in this region of the body during sleep. Over time, a person can develop a sense of comfort in response to this contact which can assist in the sleep process. Whether this is an association that develops mentally or is simply a physical response to familiar contact is uncertain. However, the favorable environment associated with pillow contact in this laterally offset location may be simulated by the back pillow without need of the full, dual pillow system.

Figure 11:
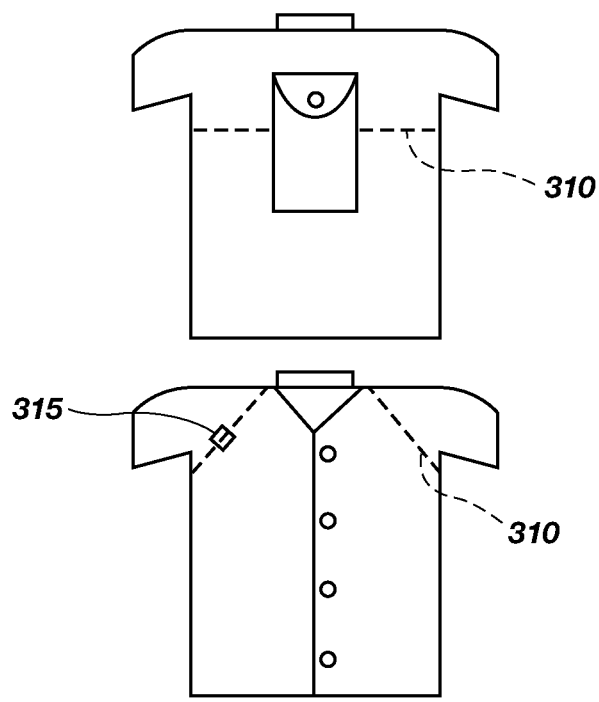
FIG. 11 illustrates a front and back plan view of a prior art night shirt having a securing member configured to minimize movement of the pillow sleeve and pillow while worn by a user.

As illustrated in FIG. 5 showing an individual 52 lying on a bed 50 on his right side, the back pillow 53 provides this contact when positioned in a similar manner and location as shown in the drawings. This occurs when the pillow 53 is essentially worn with the pajamas, tank top or night gown 54 or is otherwise similarly attached to the individual's body. This is accomplished by suspending the light weight pillow 53 from an attachment location by a hinge attachment member 58 extending from and generally parallel with the spine of the individual. This attachment member 58 may be a single connecting hinge 160 (FIG. 8), or a single sewn line of attachment between the shirt 54 and the pillow sleeve 56 which forms a rotational axis to the pillow. Similarly, the hinge structure can include several sewn lines of attachment between the shirt 54 and the pillow sleeve 56 which form a hinge member as shown in FIG. 11, in which loose material of the shirt provides slack between the shirt and pillow to allow a hinge-like rotation.

When attached at the this area, the pillow can then displace to either the right or left side, depending upon which side the individual selects as a sleeping side. Because of the attachment member location 58 on the side of the pillow, the pillow body will hang down and in contact or near contact with both the appropriate back side of the individual and the bed surface 59. Reference to attachment at the side or along an edge of the pillow generally refers to attachment at a single edge of the pillow which preserves a hinge function to the pillow. Whereas some prior art devices are attached to night shirts or pajamas, such attachment is often at multiple sides of a pocket or pad which are substantially separated in distance, thereby restraining and limiting their rotational movement. The present invention, however, favors such rotational hinge action in order to facilitate displacement of the pillow to opposing sides of the spine as the user turns between left and right side sleeping positions. Therefore, although an attachment strip 48 or 58 may have several locations of fixation to the pillow (sewing or adhesive, etc.) the strip itself represents a single attachment edge because it preserves the desired hinge function along an edge of the pillow.

The attachment member may be with a strip of Velcro®, snaps, fasteners, sewn fabric or any other convenient attachment means capable of coupling the pillow at the individuals back. In addition to supplying a key frame of reference contact 51 at the individuals back and thereby simulating the side-sleeping environment conditioned within the POSA methodology, the location of the back pillow impedes movement of the individual to a supine sleeping position. Because the pillow is attached at an edge of the cylindrical pillow body, it will hang under force of gravity toward the bed surface. This causes rotation of the pillow 53 and its longitudinal axis 55 downward and away from a central 62 or spine reference point, and into resting contact or near contact with the laterally offset portion of the individual's back 51, proximate to the bed surface. Typically, a portion of the bed clothing will fall downward with the pillow as illustrated, adjusting the pillow location even more toward the laterally offset back region as shown. When the individual attempts to roll into a supine position, the pillow is captured between the bed 50 and the laterally offset back portion at 51, blocking further rotation of the body.

Another advantage of this invention occurs upon initial contact of the user with the pillow upon attempting to rotate into a supine position. When a light weight, balloon or inflated resilient pillow 53 is used as disclosed hereafter, the initial contact and resistance is very gentle, with the balloon component 57 within a sleeve 56 compressing slightly and avoiding an abrupt force on the individual's back. As the gentle contact intensifies with continued movement, the increasing resistance of the pillow is usually sufficient to urge the body back to a side-sleeping orientation without waking the person. Thereafter, the pillow again assumes its hanging or suspended configuration, lying near or against the laterally offset portion of the back and in contact with the bed.

A further benefit of the present invention arises with the hinge aspect of the attachment to the bed clothing or support band. With the pillow attached near the spine in a central location 62, the individual may shift from one side to another and the pillow will automatically gravitate to the appropriate right or left side, laterally offset location. Specifically, under force of gravity the pillow will fall between alternating and opposing laterally offset contact positions at the individual's back based on the side sleeping position selected—whether on the right or left side. For example, if the person represented in FIG. 5 on his right side were to shift to the left side in contact with the bed, the pillow and attached clothing would fall to the opposing left side, displacing the contact point 51 to the left of centerline 62. Based on this feature of the invention, the pillow automatically makes adjustment and is effective for both right and left side-sleeping positions, impeding rotation of the body to a supine position upon capture of the pillow between the bed 50 and opposing lateral portions of the back side of the individual adjacent to the bed.

Figure 6:
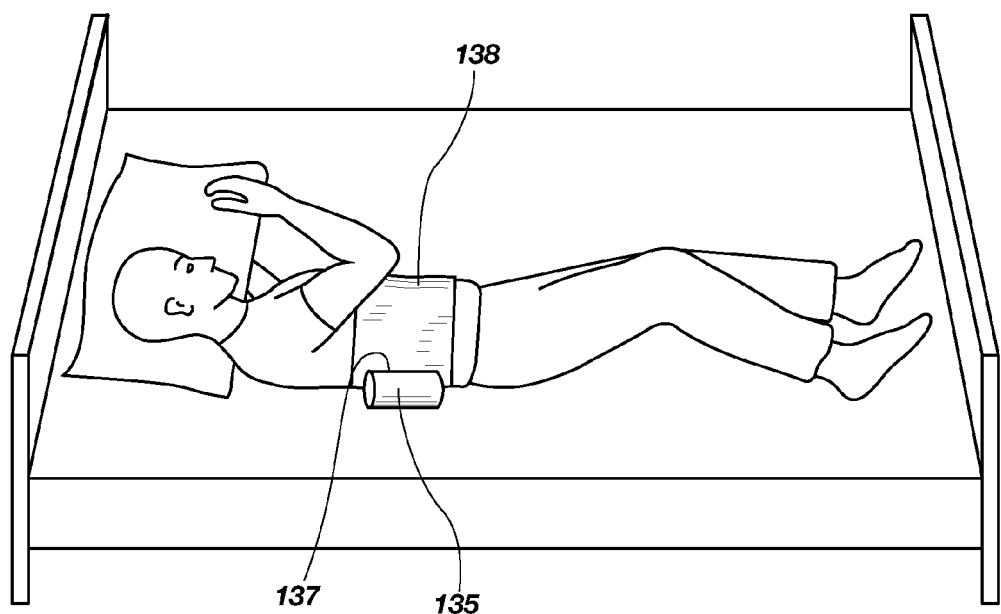
FIG. 6 depicts a perspective view of an additional embodiment of the back pillow utilizing a body band for supporting the back pillow.
Figure 7:
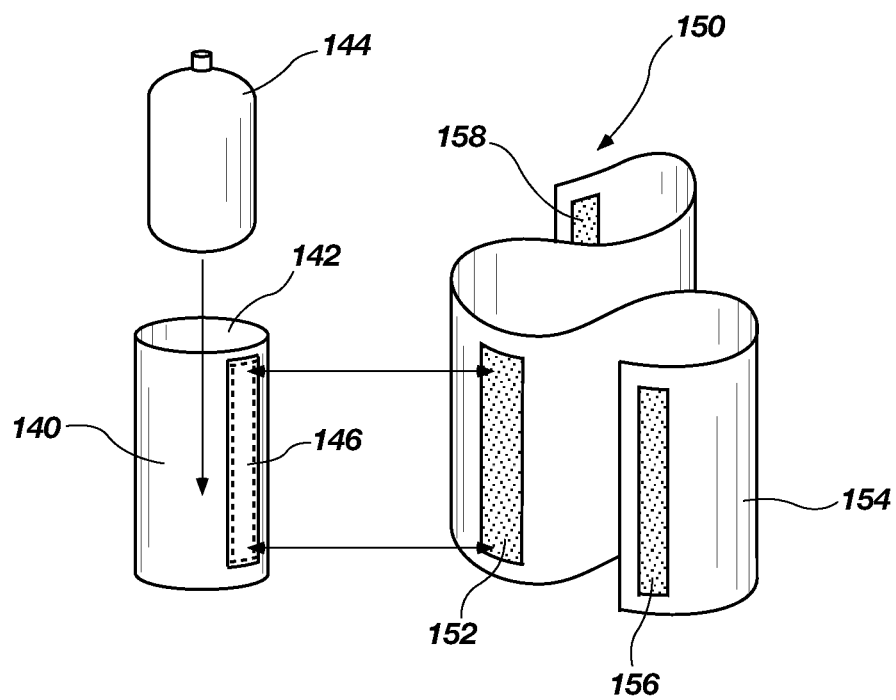
FIG. 7 shows isolated perspective views of the separated body band and pillow.

FIG. 6 illustrates an alternate method of attachment, wherein the elongate pillow 135 is suspended from a support band 138 worn around the trunk of the individual. Velcro® or other attachment means 137 can be used to attach the pillow. The band can be a fabric girdle or other form of wrap that can be vertically positioned along the torso to place the pillow at a desired location. One embodiment is shown in FIG. 7 wherein the band 150 comprises a fabric material having opposing Velcro® attachment members 156 and 158 at opposing ends to secure it to the individual. An additional attachment member 152 enables fixation of the pillow and is positioned at an intermediate location suitable for alignment with the spine of the user.

This embodiment includes a two-piece pillow configured to be very light in weight and simple in construction, as light as 1 to 3 ounces. It comprises a sleeve member 140 having an interior open space 142 and configured in a desired shape suitable for the back pillow. The dimensions of the sleeve will typically be between six and eighteen inches in length, with a diameter of three to eight inches. The sleeve can be fabricated of flexible, light weight material such as polymer or natural fabric. A complementary attachment member 146 is formed along one edge of the sleeve for receiving the attachment member 152 of the body band.

A balloon component 144 is positioned within the open space of the sleeve member and provides resilience to the pillow. Ideally, the balloon component conforms to the cylindrical shape of the sleeve when inflated. By using these materials, the pillow has a very low mass of less than 12 ounces, and ideally less than 5 ounces. A cotton fabric sleeve of 12 inch length and 4 inch diameter and an inflated interior balloon was very effective and had a total weight of less than 2 ounces. With this light weight character, the user hardly notices the presence of the pillow at his back.

This minimal weight can best be realized in an embodiment wherein an un-inflated elongate balloon is inserted within the sleeve and inflated to fill the open space. For transport and storage, the balloon pillow requires less than three cubic inches of space and is of nominal weight. The sleeve, in combination with the inflated balloon, forms a light weight balloon pillow capable of supplying the desired POSA contact reference point on the laterally offset portion of the back, as well as functioning to maintain the person in a side sleeping position against unconscious attempts to shift to a supine orientation. This compact and light weight feature allows the device to be transported conveniently under virtually any circumstances, particularly in situations where a standard CPAP device would be impractical.

The following discloses a method of use comprising the steps of positioning the balloon pillow at the laterally offset portion of the individual's back and providing a gradual cushioned resistance response through gentle compression of the balloon component as the individual attempts to rotate to a supine position. In accordance with this method, the pillow provides (i) a gradual gradient increase of resistance against rotation of the individual to minimize discomfort while (ii) gently restoring the individual to the desired side-sleeping orientation. This gradual gradient increase commences at a null point of resistance so that the body is barely to register a sudden incidence of contact with the pillow. This gradient remains low to maintain a high level of comfort to the individual as contact pressure increases. By avoiding a sudden contact force when rolling to the supine position, the body appears to be able to generally register the contact and resume the side sleeping position without arousing or awakening the sleeper. This is accomplished by using a balloon component in which the skin of the balloon (such as a party balloon) is very thin and remains pliable under pressure to conform to the body shape, based on a sufficiently low air pressure within the balloon. This is in contrast to other prior art structures having somewhat rigid outer skin structure that is less pliable and with which body contact serves to alert the individual of immediate contact.

The embodiments discussed thus far share a common characteristic of angular adjustment or hinge action about the attachment location and/or spine of the user. In the case of the pillow and attached bed clothing, the angular rotation of the pillow occurs in part because of the typical loose nature of bed clothing as shown in FIG. 5, in combination with allowed movement of the attachment member 58. The amount of displacement will usually be a matter of taste for the individual, but is preferred to be at least 5 degrees of movement with respect to a central reference point identified as 62. Greater angular rotation can be applied to increase the displacement away from the spine and into close contact with the bed. Accordingly, when located approximately centrally at the back of the individual, the pillow is adapted to automatically adjust to a side-sleeping orientation on either a left or right side.

Generally, therefore, one embodiment of the present invention can be described as a light weight, elongate pillow having a longitudinal axis and being configured to rest at a back side of the individual when reclined in a side-sleeping orientation on the bed, the pillow including attachment structure positioned along a longitudinal edge of the pillow to secure the pillow to the individual, the attachment structure having sufficient flexibility to allow the pillow to rotate with respect to and rest against the individual's back to a laterally offset, suspended configuration in general alignment with the individual's spine. Ideally, the rotation of the pillow should be at least 5 degrees of angular rotation with respect to and away from the spine, and as much as 45 degrees, where a separate hinge member is provided.

Figure 8:
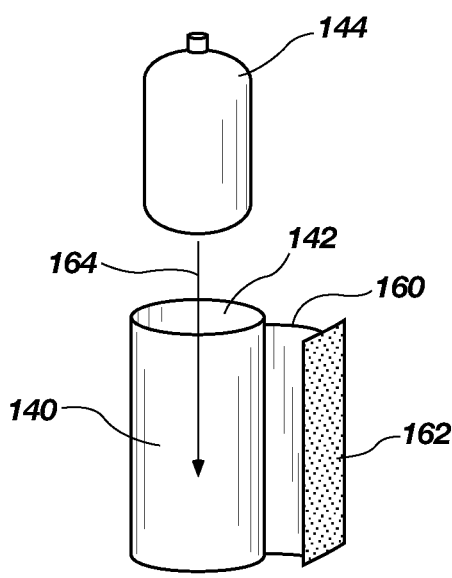
FIG. 8 is a perspective view of a pillow sleeve with attached hinge member illustrating insertion of a balloon member for inflation therein.

FIG. 8 illustrates a form of attachment which includes a flexible, light weight hinge component 160 coupled to the pillow sleeve at one side and to the attachment member 162 on the other side. The material composition of the hinge member is preferably thin and flexible to provide for unimpeded rotation of the pillow and its elongate axis 164 with respect to the spine. The length of the hinge component may extend at least a quarter inch from the pillow edge but at no greater length than will allow the pillow to fall to the laterally offset contact position at the individual's back based on the individual's size, providing an extended radius of rotation to the pillow member to position the pillow to a suspended rest position in contact with the individual's back and proximate to the bed. In other words, there should not be a significant amount of slack in the attachment member 160 when it is resting on the bed surface and in contact at the individual's back. Such slack would allow the pillow to migrate away from the desired contact position with the individual as shown in the drawings.

For example, an individual of average size may have require a hinge member of only up to one inch in length, whereas a person of very large stature may need a greater length, depending upon the diameter of the pillow and softness of the mattress on the bed. It will be apparent that a soft mattress will allow the person to sink into the mattress body, increasing the proximity to the suspended pillow and thereby decreasing the length of the hinge member. Ideally, the pillow should fall to a position in contact with the individual's back and in slight contact with the bed surface. Accordingly, the back pillow may require tailoring in size to the body dimensions of the user in order to properly function as disclosed, resulting in the desired "partial" capture of the pillow between the laterally offset back area and the bed when the individual attempts to rotate to a supine position.

As shown in FIG. 8, the attachment member 162 may be coupled directly to a mating attachment member on either bed clothing 54 or a body band 138. Various mechanisms for attachment will be apparent to those skilled in the art. The selection of materials may include numerous structures and configurations, including a continuous hinge member as shown in the drawing, or alternatively, connecting straps, strings, tabs, films and similar flexible materials. A thin fabric material such as nylon, silk or light weight cotton effectively provides the benefits of a substantially resistance-free aspect. It should also be noted that the balloon/sleeve combination can be integrated into a single structure wherein the balloon is formed of the fabric material. In this case, the fabric is sized and cut to form the inflated component when sealed in a bladder configuration. The hinge member 160 may simply be formed from an unsealed, extended edge of the fabric material. This eliminates the need for the separate sleeve portion of the pillow, and provides a connecting hinge element 160 that can be sewn directly to the shirt or night gown. Other integrated bladder constructions will be apparent to those skilled in the art, based on the principles set forth herein.

With the hinged embodiment, the pillow will hang lower towards the bed and may apply slightly more contact pressure at the user's back than is acceptable, particularly if partially captured between the bed and offset back area. This can readily be resolved by the user reaching behind the back and releasing the captured pillow from between the bed and back side of the individual by slightly tilting or displacing the pillow away from the back to a "partial" captured, resting position on the bed. Although there may be a slight contact at the offset back side, the nominal weight of the pillow is substantially unnoticeable when it is resting primarily on the bed. Accordingly, this last step provides a static, non-supine sleep condition with nominal contact pressure by the pillow on the individual for maximum comfort.

FIG. 10 originally disclosed in the parent Zohlmann patent application, together with FIG. 5 of the parent North application, further illustrates the described hinge concept as set forth above. As shown in these figures, the desired partial capture condition can be realized by rotation of the pillow 203 and its longitudinal axis 55 downward and away from a central 62 or spine reference point, and into resting contact or near contact with the laterally offset portion of the individual's back 51, proximate to the bed surface 222.

FIG. 10 is a prior art view of user 224 lying on the bed 222 and moving to a side position by rotating in direction 227. In the side sleeping position, the attachment member 58 reflects a hinge aspect which enables the pillow sleeve 204, with the pillow, or insert 203, to rotate in the direction 229 and achieve a position at the bed and lower shoulder. When taken in combination with the disclosure of the North application, with discussion of the partial capture concept, one can envision a hinge member 58 which is modified to achieve a result similar to the hinge member 160 of FIG. 5.

FIG. 11 illustrates a front and back view of a prior art night shirt, according to one embodiment of the invention. The night shirt includes a securing member 310 configured to provide a user with a better fitting night shirt. The securing member 310 is further configured to minimize movement of the night shirt on a user, and thereby minimize movement of the pillow sleeve 204. In at least one aspect, minimizing movement of the night shirt and pillow sleeve 204 assists in maintaining the pillow sleeve 204 and pillow in the proper orientation with the desired partial capture for prevention of movement to a supine sleeping.

Shown in FIG. 11, the securing member 310 is coupled to a portion of the night shirt, such as, but not limited to, the pillow sleeve 204 and extends around both sides of the shirt to the front of the night shirt. It is contemplated that the securing member 310 may comprise a variety of materials and configurations. In one non-limiting example, the securing member 310 is an elastic member that extends from the pillow sleeve 204 to the front of the night shirt. In an additional embodiment, at least portion of the securing member Further, the securing member 310 may be internalized into the night shirt, such that at least a portion of the securing member 310

In a further embodiment, the securing member 310 includes an adjustment device 315, the adjustment device 315 configured to enable a user to increase or decrease the tension of the securing member 310, thereby adjusting fit of the night shirt around the user. In a non-limiting example, the adjustment device 315 is disposed on the frontal portion of the night shirt, such that a user may quickly and easily adjust the fit of the night shirt.

Figure 12:
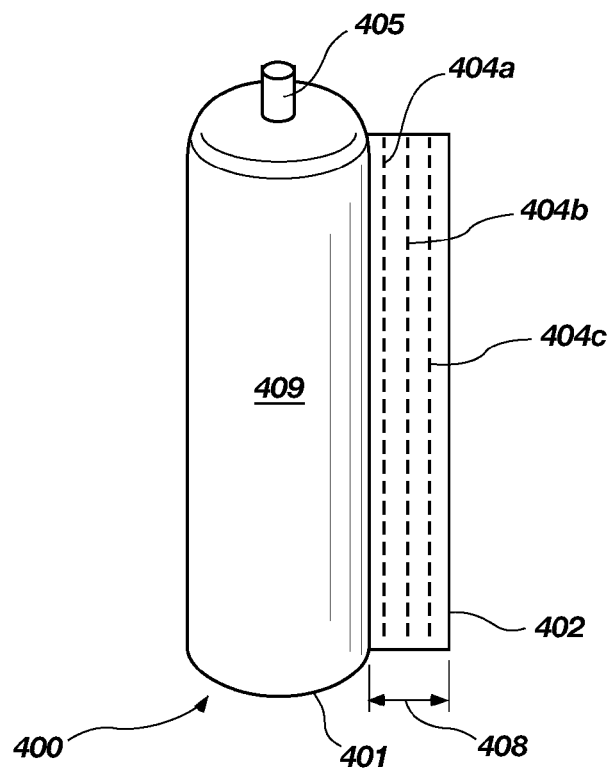
FIG. 12 is a perspective view of another embodiment of the present invention as a back pillow with attachment tab.

An additional embodiment of this invention is shown in FIG. 12 wherein the back pillow is formed as a single structure from fabric. A desirable fabric would include an exterior or sleeve surface 409 of the pillow having a frictional surface which resists migration from the contiguous contact based on resistive contact at the bed surface. In other words, the pillow and bed sheet are maintained in proximity to the user's back based on friction between the pillow surface and bed surface.

A bladder component 401 is prepared by sealing two opposing sheets of impermeable fabric in a perimeter pattern that creates a cylindrical, inflatable pillow member. An appropriate fill valve 405 is provided to enable the user to blow into the pillow to inflate to a desired pressure level. An attachment tab 402 is formed at one edge of the pillow to enable attachment to the user's bed clothing as described above, forming a suspended configuration suitable to realize the desired partial capture at the juncture of the user's back and bed surface. This tab can be readily formed by having extra material extend beyond the sealed perimeter prior to fabrication, leaving this flat, uninflatable section to form the attachment tab as shown.

Figure 13:
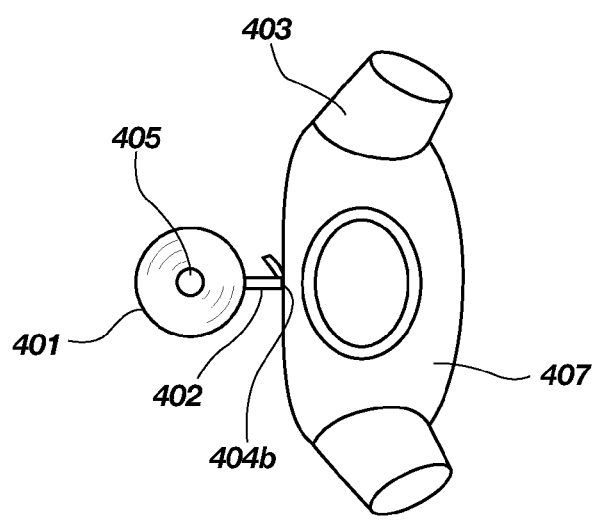
FIG. 13 shows a top plan view of the embodiment of FIG. 12 attached to a shirt.
Figure 14:
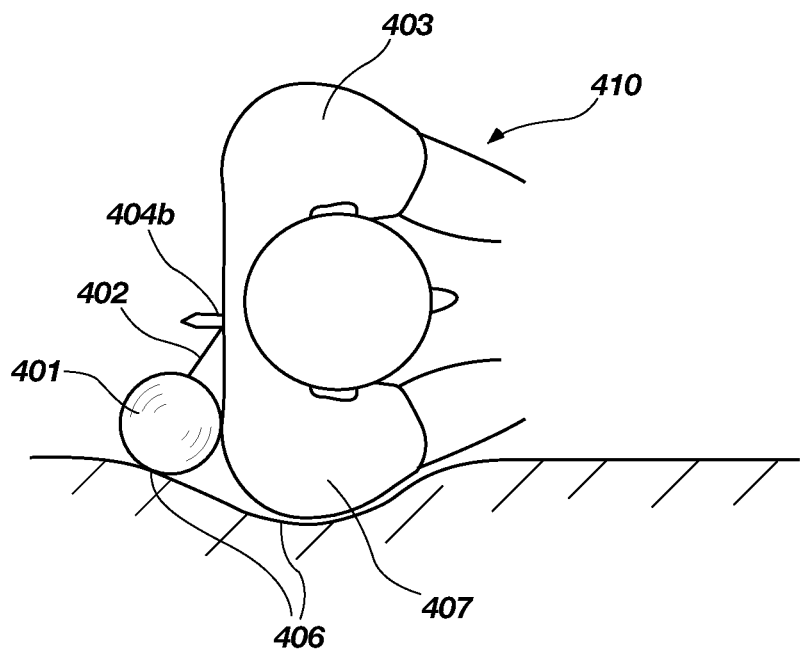
FIG. 14 illustrates a top plan view of the shirt and back pillow of FIG. 13 in use on a bed surface.

The length 408 of the tab may be selected to fit the specific size of the user. Greater lengths will be needed for a larger physical frame in order to properly position the pillow at the partial captured location as shown in FIG. 14. A more specific adjustment of length can be accomplished by selecting one of the indexed markings 404a, b, or c as the point of attachment to the bed clothing. For example, FIG. 13 illustrates shirt 407 with a point of attachment of the tab 402 at index mark 404b. This selection could be based on positioning the unattached pillow 401 in the proper configuration of "partial capture" as shown in FIG. 14, then while holding the pillow in place, extending the tab 402 upward to the location of the user's spine to identify the correct tab length. The index markings can be used as a reference to identify the proper point of attachment, sized precisely to the user's frame. Once determined, d, the tab can be sewn, pinned, clipped or otherwise affixed to the bed clothing at the index mark, such as 404b. As shown the proper partial capture configuration depends upon the frame size and weight of the individual 410, the indentation of this person into the mattress 406 and the circumference of the pillow 401. The use of the indexing marks and adjustment of length of the tab enable anyone to properly establish this desired partial captured configuration.

Figure 15:
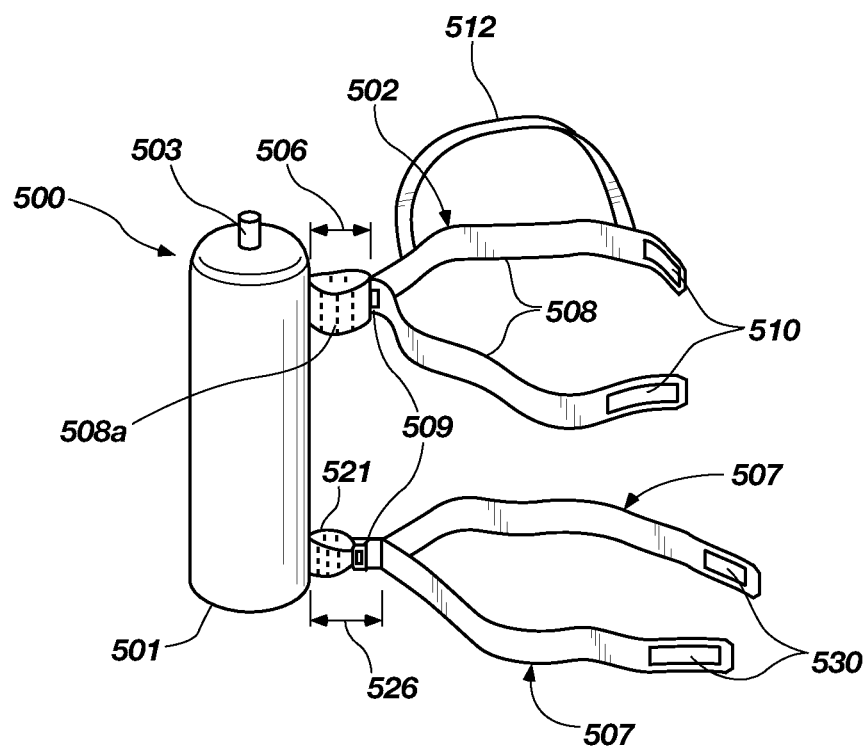
FIG. 15 depicts a perspective view of a further embodiment of this invention illustrating a back pillow with attachment straps.
Figure 16:
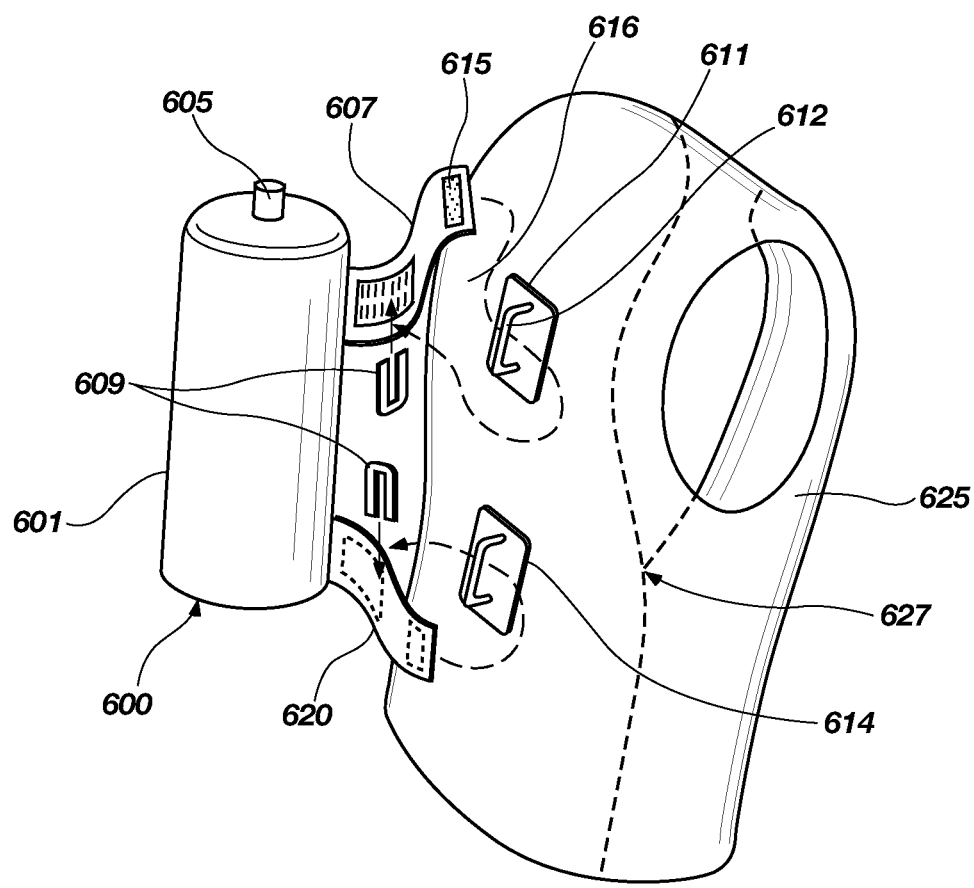
FIG. 16 provides a perspective view of a vest embodiment of the present invention.

FIGS. 15 and 16 illustrate other embodiments which permit the person to make their own sizing adjustment experimentally. FIG. 15 shows a back pillow 500 having an inflation valve 503 and an attached pair of straps 502 and 507. In order to achieve the correct tab length 506, indexing marks 508a may be provided as referenced above. A clip, pin, snap or other connecting means 509 is applied along the straps 502 at the correct length to establish a tab length specific for this individual. The remaining ends 508 of the straps are now free to wrap around the chest of the user, to be fastened at a comfortable tightness by Velcro or other fastening means 510. It will be apparent that a shoulder strap 512 or harness could also be used in place of or in combination with the chest strap shown in the drawing to prevent the pillow from migrating down the users back during sleep.

The lower strap 507 can be similarly adjusted to realize the proper length 526 for positioning at a lower portion of the user's trunk. Frequently, this tab length 526 will differ from the length 506 of the upper strap because the upper trunk is usually larger in circumference than the lower trunk. Therefore, the lower length 526 may need to be greater than that of the upper strap 506. To make these exact adjustments, the user would estimate the tab lengths 506 and 526 and position the clip 509 in place. The pillow and straps would then be placed on the person, who would then lie on his bed as if he were asleep. Based on the softness of the mattress and the weight and frame size of the individual, the user would change the clip 509 position on the straps until each tab length 506 and 526 was correct in order to realize the partial captured condition of the pillow as shown in FIG. 14. It will be apparent that a combination of attachment tab 402 and straps 505 can be used as well. Fastening means 530 are shown for securing loose ends of the strap 507 together to allow an individual to adjust the pillow position with respect to the desired captured condition.

FIG. 16 illustrates a vest-type embodiment which offers greater stability in positioning the back pillow on a stable platform at the user's back. The pillow 600 is similar in construction to the previous pillows illustrated and includes s cylindrical body 601 and fill valve 605. Straps 607 and 620 will be used to attach the pillow to mounting loops 611 and 614 on the back of the vest. The same positioning steps can be applied as described above, with the straps 605 and 620 being adjusted in length by fastening the loose end through loop opening 612 and attaching it to the interior section of the strap 616 with Velcro or other fastening means. The user then tests the positioning of the pillow in the side position on the bed, snaking further adjustments in the length to optimize the position. The vest 625 can be comfortably fastened 627 in the front to retain this configuration through the night.

It is to be understood that the foregoing examples and illustrations are merely representative of various embodiments which are comprehended by the following claims and are not, therefore, to considered limiting except as required to sustain validity of the claims.

I claim:

1. A method for developing a positional orientation sleep aspect (POSA) to enhance individual awareness of sleeping position to enable the individual to assume and maintain at least one preselected side-sleeping orientation alternately on either a left or right side on a bed surface and thereby avoid a supine position, said individual contact on the bed surface providing a first contact point of reference to a side-sleeping orientation for the individual, the method comprising the steps of:
   a) attaching a light weight, elongate back pillow at the back side of the individual in a hinged, rotatable, suspended configuration that provides concurrent contact of the pillow with both a lateral back side of the individual and the bed surface when the individual is in a side sleeping orientation and in a manner that provides a second contact point of reference to the individual in the side-sleeping orientation;
   b) positioning a second pillow at a contact point on a leg of the individual in accordance with POSA methodology to establish a third contact point of reference for the side-sleeping orientation; and
   c) rotating the back pillow to an opposing lateral back side of the individual as the individual repositions to an opposing side-sleeping position to maintain the second contact point of reference at the individual's back;
   d) wherein the step of attaching the light weight, elongate pillow at the back side of the individual in the suspended configuration comprises (i) securing a lower end of the elongate back pillow to at least one support strap worn around the trunk of the individual and (ii) laterally adjusting a position of the strap and attached pillow to properly position the pillow in the partial capture configuration concurrently at the back and bed surface with the user in the side-sleeping position.

2. A method as defined in claim 1, further comprising the steps of (i) suspending the light weight pillow with a hinge component from an attachment location extending from and generally aligned with the spine of the individual; and (ii) rotating the pillow and its longitudinal axis at the hinge component under force of gravity between alternating and opposing laterally offset contact positions at the individual's back in partial capture while the pillow is concurrently in contact at contiguous locations of the user's back and bed surface when the user is in a side sleeping orientation for impeding rotation of the body to a supine position.

3. A method as defined in claim 1, wherein the step of attaching the light weight, elongate pillow at the back side of the individual in the suspended configuration comprises attaching the elongate pillow to bed clothing worn by the individual by use of a hinge tab coupled between the pillow and the bed clothing.

4. A method as defined in claim 1, further comprising the steps of (i) forming the light weight pillow by selecting a sleeve member having an interior open space and configured in a desired shape for the back pillow, (ii) inserting a bladder component within the open space of the sleeve member, and (iii) inflating the bladder component within the sleeve member to fill the open space and form a light weight balloon pillow to support the sleeve against substantial collapse under weight of the individual.

5. A method as defined in claim 4, further comprising the steps of positioning a balloon pillow at the individual's back in accordance with claim 1 and providing a gradual cushioned resistance response through gentle compression of the balloon pillow as the individual attempts to rotate to a supine position wherein (i) the pillow provides a gradual contact pressure gradient increase between the pillow and the individual's back commencing at an initial null point of resistance against rotation of the individual to minimize discomfort (ii) increasing the resistance against rotation of the individual as the balloon pillow is compressed by weight of the individual, and (iii) gently restoring the individual to the desired side-sleeping orientation by applied pressure from the balloon pillow.

6. A method as defined in claim 1, further comprising the step of positioning the second pillow, unconnected with the first pillow, to a position in contact with at least one of the individual's legs, thereby establishing the three concurrent contact points of reference using the individual's side, back and legs.

7. A device for enabling an individual located on a bed to sustain a side-sleeping orientation on either a left or right side, said device comprising:
a light weight, elongate pillow having a longitudinal axis and being configured to rest at a lateral back side of the individual when reclined in a side-sleeping orientation on the bed; said pillow including an attachment structure to secure the pillow to the individual, said attachment structure including a flexible, light weight, hinge component coupled to the pillow at an exterior edge of the pillow to provide substantially unimpeded rotation of the pillow with respect to the spine, wherein the hinge component has sufficient flexibility to allow the pillow to bi-directionally rotate in opposite directions to rest against the individual's back at laterally offset, partially captured contact positions and in contiguous, concurrent contact with an adjacent bed surface, while the user remains in a side-sleeping orientation; and
a strap attached in fixed position near a lower end of the pillow and having a length for positioning around a lower portion of the individual's trunk to enable the individual to reposition the attached pillow by displacing the strap left or right to position the pillow at the partially captured contact position at either the left or right side of the individual, said strap further including fastening means for securing loose ends of the strap together around the trunk.

8. A device as defined in claim 7, said attachment structure having an adjustable connecting length from the pillow exterior edge to the individual's bed clothing to enable rotation of the pillow to right and left sides of the individual to the partially captured condition wherein the pillow is neither fully captured nor fully suspended with respect to the individual and wherein the attachment structure comprises at least one laterally projecting tab coupled to the pillow and extending from the pillow along an edge parallel with a central axis of the pillow, the at least one tab including means for attachment to bed clothing of the individual at a length which provides the partially captured contact position.

9. A device as defined in claim 8, wherein the laterally projecting tab includes indexing marks positioned parallel with the elongate central axis of the pillow to provide reference points for attachment of the tab to the individual with an appropriate hinge length to facilitate the partial capture contact between the user and contiguous pillow and bed surface.

10. A device as defined in claim 7, wherein the attachment structure comprises (i) bed clothing worn around the trunk of the individual and (ii) an attachment member coupled between the bed clothing and the elongate pillow, the combination of clothing and attachment member being configured to provide the sufficient flexibility to allow the pillow to rotate with respect to the individual's spine and rest against the individual's back to a laterally offset, suspended configuration in general alignment with the individual's spine.

11. The device as defined in claim 10, wherein the attachment structure couples to the bed clothing at both upper and lower ends of the pillow to form the hinge component.

12. The device as defined in claim 7, wherein the hinge component member includes a hinge length that extends at least a quarter inch from the pillow edge but at no greater distance than will allow the pillow to fall to the laterally offset contact position at the individual's back based on the individual's size, providing an extended radius of rotation to the pillow member to position the pillow to a suspended rest position in contiguous contact with the individual's back and proximate to the bed.

13. The device defined in claim 7, further comprising a three-point reference contact POSA sleep system including a second pillow, such as a knee pillow, to provide a third contact point of reference for side-sleeping orientation in combination with the (i) individuals' side contact with a bed surface and (ii) contact of the elongate pillow at the lateral back side of the individual.

14. A device as defined in claim 7, comprising a light weight pillow formed by a sleeve member having an interior open space and configured in a desired shape for the back pillow and an inflated balloon component within the open space of the sleeve member to fill the open space and form a light weight balloon pillow to support the sleeve against substantial collapse under weight of the individual.

15. A device as defined in claim 7, wherein the attachment structure coupled to the pillow at the exterior edge of the pillow includes a second strap for attachment to an upper trunk portion of the individual, the combination of upper and lower straps providing attachment structure for the pillow to the individual and for proper positioning of the pillow at the lateral back side position.

16. A device as defined in claim 7, wherein an exterior surface of the pillow includes a frictional surface which resists and prevents migration of the pillow along the bed surface and away from the contiguous contact based on resistive contact at the bed surface.

17. A device for enabling an individual located on a bed to sustain a side-sleeping orientation on either a left or right side, said device comprising:
an elongate pillow having a longitudinal axis and being configured to rest at a back side of the individual when reclined in a side-sleeping orientation on the bed; and an attachment member for supporting the pillow at the individual's back including a flexible, light weight hinge component including a rotational hinge axis and being coupled to the pillow along a pillow edge substantially aligned with the longitudinal axis and configured to allow the pillow to fall freely into contact at either a laterally offset left or right back side of the individual when the individual is lying on the respective left or right side; and a strap attached in fixed position near a lower end of the pillow and having a length for positioning around a lower portion of the individual's trunk to enable the individual to reposition the attached pillow by displacing the strap left or right to position the pillow at the partially captured contact position at either the left or right side of the individual, said strap further including fastening means for securing loose ends of the strap together around the trunk.

18. A device as defined in claim 17, wherein the hinge component has a length from the pillow of at least a quarter inch from the pillow edge but at no greater length than will allow the pillow to fall to a laterally offset contact position concurrently at the individual's back and contiguous bed surface, based on the individual's size and weight and corresponding indentation at a contacted surface of the bed.

\* \* \* \* \*